United States Patent [19]
Alini et al.

[11] Patent Number: 5,872,265
[45] Date of Patent: Feb. 16, 1999

[54] METHOD FOR PREPARING COUMARIN AND DERIVATIVES THEREOF

[75] Inventors: Stefano Alini, Cava Manara; Livius Cotarca, Torviscosa; Pietro Delogu, Trieste, all of Italy

[73] Assignee: Industrie Chimiche Caffaro S.P.A., Milan, Italy

[21] Appl. No.: 809,189

[22] PCT Filed: Jul. 11, 1995

[86] PCT No.: PCT/EP95/02687

§ 371 Date: Mar. 17, 1997

§ 102(e) Date: Mar. 17, 1997

[87] PCT Pub. No.: WO96/09298

PCT Pub. Date: Mar. 28, 1996

[30] Foreign Application Priority Data

Sep. 20, 1994 [IT] Italy ................................. MI94A1908

[51] Int. Cl.$^6$ ................................................. C07D 311/08
[52] U.S. Cl. ........................... 549/290; 549/289; 549/285
[58] Field of Search ..................................... 549/290, 289, 549/285

[56] References Cited

U.S. PATENT DOCUMENTS 3,523,125  8/1970  Theissen et al. ..................... 260/397.2

FOREIGN PATENT DOCUMENTS 57-14759  9/1982  Japan .

*Primary Examiner*—Amelia Owens
*Attorney, Agent, or Firm*—Henry D Coleman; R. Neil Sudol

[57] ABSTRACT

A process for producing coumarin and substituted coumarins starting from substituted hexahydrocoumarins or from substituted dihydrocoumarins. The process includes dehydrogenation in the presence of catalysts based on metals of Group VIII of the periodic table of the elements and in the presence of at least one easily reducible organic compound. The invention allows to achieve exceptionally high yields that do not require the recycling of the hexahydrocoumarin or of the dihydrocoumarin that are present at the end of the reaction, and also allows to achieve high selectivity and easy purification.

20 Claims, No Drawings

METHOD FOR PREPARING COUMARIN AND DERIVATIVES THEREOF

The present invention relates to a new process for producing coumarin and substituted coumarins starting from substituted hexahydrocoumarins or from substituted dihydrocoumarins.

Coumarin compounds are widely used in the field of perfumes, flavoring agents, dyestuffs, and as intermediate products for agricultural and pharmaceutical products.

It has been known since the last century that coumarin can be prepared by condensing salicylaldehyde with ethanoic anhydride in the presence of sodium ethanoate (Perkin, J. Chem. Soc. 21, 53, 1868). Coumarin is currently produced industrially by using the Perkin reaction, modified appropriately to improve yields.

U.S. Pat. No. 2,204,008 describes a process for preparing coumarin in which the salicylaldehyde, the ethanoic anhydride, and the sodium ethanoate, in a ratio of 1:2:2 respectively, are heated to 150° C. in the presence of salts of Co, Fe, Ni, Mn, Pt, and Pd; heating to 180°–200° C. is performed after a further addition of ethanoic anhydride and ethanoic acid. The yield obtained is 64.5%.

Austrian patents No. 272332 and 272333 describe a process for producing and purifying coumarin, again starting from salicylaldehyde and ethanoic anhydride. By appropriately varying the percentage of sodium ethanoate and raising the temperature to 210° C., 80% yields are achieved.

All these procedures have the drawback that they use an expensive reagent, such as salicylaldehyde, and use ethanoic anhydride and sodium ethanoate, and therefore problems arise in the disposal or recovery of the ethanoic acid and of the sodium salt. Accordingly, new methods for preparing coumarin that do not use salicylaldehyde have been developed.

German patent No. 2 041 563 and U.S. Pat. No. 3,878, 074, 3,859,311, 3,963,473, and 3,888,883 describe a new method for preparing coumarins starting from phenolic derivatives and vinylation thereof with acrylic derivatives. However, coumarin yields are not great (51%) and there are several by-products (Kirk-Othmer, vol. 7, page 200, 3rd ed.).

U.S. Pat. No. 3,998,851 describes a process for preparing coumarin compounds starting from o-hydroxycinnamic acid or esters thereof in the presence of metallic catalysts of Group VIII of the periodic table. In this case, too, very expensive reagents and very drastic operating conditions are used.

U.S. Pat. No. 3,891,678 describes a process for co-producing coumarin and dihydrocoumarin by dehydrogenating hexahydrocoumarin in the presence of metallic catalysts of Group VIII of the period system of elements. Co-production causes problems in the disposal of the less wanted product. There is also the need to provide means for separating and purifying the two products.

U.S. Pat. No. 3,856,819 describes the dehydrogenation of dihydrocoumarin in the presence of the same catalysts and in the presence of a flow of air. The maximum conversion that is achieved is 70%, and the catalyst undergoes a rapid deactivation process.

The recent Japanese patents JP 33153/89 and JP 197098/90 describe a process for obtaining dihydrocoumarin and coumarin by cyclization of esters of 3-(2-cyclohexanoyl)-propanoic acid or derivatives thereof and simultaneous dehydrogenation of the obtained hexahydrocoumarin, in the presence of metals such as Pt, Pd, Ru, and promoters such as barium sulfate, nickel oxide, and chromium salts.

This process has the problem of the co-production of coumarin and dihydrocoumarin and therefore of separating them to recover the products. In all the examples provided in the mentioned patents, the coumarin and the dihydrocoumarin are obtained in a molar ratio of approximately 1:1, and the production process must provide for an expensive step for separating the two products, which are marketed as pure substances. The use of refinements described in the various patents, such as feeding an inert gas or air to remove the hydrogen from the reaction environment (U.S. Pat. No. 3,856,819), executing of the reaction in vacuum (JP 277688/91), or using specifically designed catalysts (JP 494/92) is useless in shifting this ratio.

Furthermore, for pharmaceutical or cosmetic use it is indispensable to ensure that heavy metals, such as Ni and Cr, are entirely eliminated. It should also be noted that dehydrogenation is achieved in an extremely long time (30–50 hours) and with the use of high-boiling solvents, which are also difficult to separate and recover.

The present invention overcomes the above mentioned difficulties by a method that allows to obtain coumarin starting from hexahydrocoumarin or dihydrocoumarin with exceptionally high yields that do not require the recovery and recycling of the hexahydrocoumarin or of the dihydrocoumarin that are present at the end of the reaction. Furthermore, non-toxic catalysts are used and operating conditions that can be achieved with conventional apparatus.

The aim of the invention is therefore to achieve high selectivity to have a single reaction product.

Another object is to obtain a raw reaction product that is easier to purify.

Another object is to provide a process that is economically highly advantageous.

This aim, these objects, and others are achieved by the process according to the present invention for producing coumarin and derivatives thereof with formula (I):

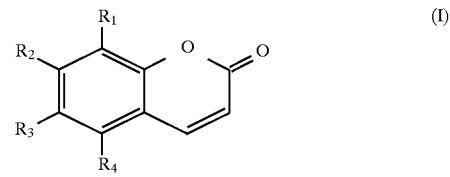

wherein each one of R1, R2, R3, and R4 is: hydrogen, alkyl, aryl alkyl, alkoxyl, halogen, or hydroxyl, by dehydrogenation of a compound with formula (II):

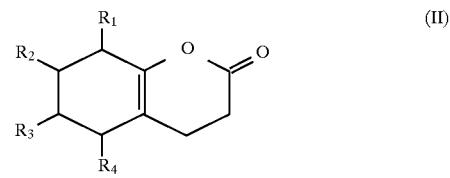

or of a compound with formula (III):

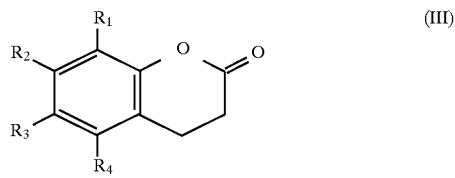

obtained by using catalysts based on metals of Group VIII of the periodic table of the elements, in the presence of at least one easily reducible organic compound.

The compound with formula (I) is preferably chosen among coumarin, 6-methylcoumarin, and 7-hydroxycoumarin.

The process is performed by dehydrogenating hexahydrocoumarin (Diagram 1) or dihydrocoumarin (Diagram 2):

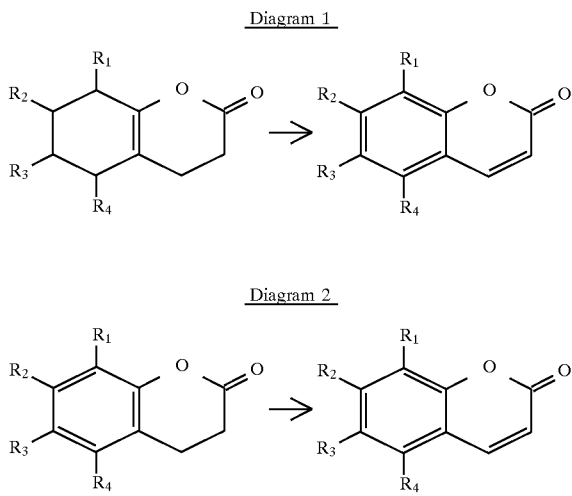

by using metallic catalysts of Group VIII of the periodic system of the elements, preferably Pt, Pd, Ru, generally supported on carbon, silica gel, alumina, barium sulfate, and so forth, in the presence of an easily reducible organic compound and optionally of an appropriate solvent. It is convenient to work with a noble metal mole percentage between 0.5 and 10% with respect to the hexahydrocoumarin. The best results are achieved with catalyst concentrations between 1% and 3%. The reaction can be performed with or without solvents. The following can be used as solvents: diphenyl ether, benzyl ether, methyl naphthyl ether, ethyl naphthalene, dimethyl diphenyl, dodecane, tetradecane, tetralin, acetophenone, phenyl propyl ketone, dimethyl glutamate, methyl or ethyl benzoate, and so forth.

It has been found that the addition of organic derivatives that can be easily hydrogenated allows to achieve coumarin yields of even 90%, with practically complete conversions of the raw material, at lower temperatures than those used in their absence and with particularly short reaction times. Among these organic compounds, the following are articularly suitable:

unsaturated olefin compounds, such as maleic anhydride, maleic acid esters, fumaric acid esters, linear olefins, and styrene;

diene compounds, such as butadiene and isoprene;

carboxylic compounds, aldehydes, and ketones, such as benzophenone and substituted benzophenones or benzoquinones.

The list of usable organic derivatives must be considered as a non-limitative example of the possibilities covered by the present invention; the choice among reducible organic compounds must be made according to considerations related to simplicity in providing the reduction reaction. Therefore, high-boiling-point compounds, which allow to perform the reaction at temperatures above 150° C. in a homogeneous phase at atmospheric pressure, such as maleic acid or diethyl maleate, are preferred but not exclusively usable. As an alternative, the reaction can be performed with low-boiling easily reducing compounds, at high temperatures and at higher-than-atmospheric pressures. The temperature can be between 100° C. and 350° C. and preferably between 180° C. and 300° C. The ratio between the easily reducible organic compound and the hexahydrocoumarin can be between 0.25:1 and 10:1, preferably between 0.5:1 and 5:1. The easily reducible compound can be present from the beginning of the reaction or can be added in a subsequent step, after part of the dehydrogenation has occurred merely due to the metallic catalyst.

The coumarin thus prepared is then recovered by filtering the catalyst and by crystallization by an appropriate solvent or mix of solvents, such as the water/ethanol mix, or by fractional distillation.

EXAMPLE 1

10 g of hexahydrocoumarin, 35 g of diethyl maleate, and 2.2 g of 5% Pd/C were loaded in a flask. The mix was heated to 220° C. for 9 hours and kept under constant and intense agitation. After aromatization had completed, the catalyst was removed by filtration and the product was recovered by fractional distillation, separating the diethyl succinate that had formed. 8.6 g of coumarin were recovered, giving a yield of 90%. The ratio between coumarin and dihydrocoumarin, at the end of the reaction, was 80:1.

EXAMPLE 2

1.5 g of hexahydrocoumarin, 5.2 g of diethyl fumarate, and 0.5 g of 5% Pd/C were loaded in a flask. The mix was heated to 220° C. for 6 hours and kept under constant and intense agitation. After aromatization had completed, the catalyst was removed by filtration and the product was recovered by fractional distillation, separating the diethyl succinate that had formed. 1.3 g of coumarin were recovered, giving a yield of 90%. The ratio between coumarin and dihydrocoumarin, at the end of the reaction, was 80:1.

EXAMPLE 3

1.5 g of hexahydrocoumarin and 0.5 g of 5% Pd/C in 20 cc of diethyl succinate were loaded in a flask. The mix was heated to 220° C. for three hours. A mix containing coumarin and dihydrocoumarin formed. By adding 3.5 g of diethyl maleate only at this point, and by continuing to apply heat for four more hours, coumarin was obtained as prevalent product, with an isolated-product yield of 65%. The ratio between coumarin and dihydrocoumarin, at the end of the reaction, was 3:1.

EXAMPLE 4 (for comparison)

1.5 of hexahydrocoumarin and 0.5 g of 5% Pd/C in 20 cc of diethyl succinate were loaded in a flask. The mix was heated to 220° C. for three hours. A mix containing coumarin and dihydrocoumarin formed. By continuing to apply heat, the ratio tended to reach an equilibrium condition, in which the prevailing product was dihydrocoumarin and the ratio between coumarin and dihydrocoumarin was 1:3.

EXAMPLE 5

1.5 g of dihydrocoumarin, 5.2 g of diethyl maleate, and 0.5 g of 5% Pd/C were loaded in a flask. After dehydrogenation was completed, the catalyst was removed by filtration and the product was recovered by fractional distillation, separating the formed diethyl succinate. 1.35 g of coumarin was recovered, giving a yield of 90%. The ratio between coumarin and dihydrocoumarin, at the end of the reaction, was 80:1.

We claim:
1. Process for preparing a compound with formula (I):

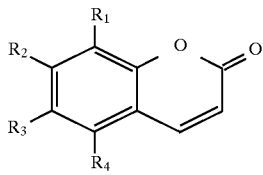

wherein each one of R1, R2, R3, and R4 is: hydrogen, alkyl, aryl alkyl, alkoxyl, halogen, or hydroxyl, by dehydrogenation of a compound with formula (II):

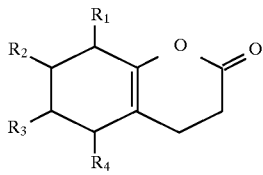

or of a compound with formula (III):

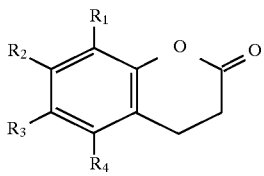

obtained by using catalysts based on metals of Group VIII of the periodic table of the elements, in the presence of at least one easily reducible organic compound.

2. Process according to claim 1, wherein said compound with formula (I) is chosen among coumarin, 6-methylcoumarin, and 7-hydroxycoumarin.

3. Process according to claim 1, wherein said easily reducible organic compound is an ester of maleic acid or an ester of fumaric acid.

4. Process according to claim 1 wherein the compound with formula (I) is recovered by crystallization or distillation of the reaction mix.

5. Process according to claim 1, wherein said dehydrogenation is achieved by using metallic catalysts.

6. Process according to claim 1, wherein said dehydrogenation of the compound with formula (II) or of the compound with formula (III) is performed at a temperature between 100° C. and 350° C.

7. Process according to claim 4, wherein said dehydrogenation is achieved with a molar ratio between said compound with formula (II) or said compound with formula (III) and said easily reducible organic compound that is between 1:0.25 and 1:10.

8. Process according to claim 4, wherein said compound with formula (II) or said compound with formula (III) is dehydrogenated in a first reaction step in the absence of said easily reducible organic compound, and wherein said organic compound is added at the end of said first step in a molar ratio between 0.5:1 and 10:1, with respect to the compound with formula (II) or to the compound with formula (III) that is initially present.

9. Process according to claim 1, wherein said reducible organic compound is selected from the group consisting of olefin compounds, diolefin compounds, carbonyl compounds and benzoquinone compounds.

10. Process according to claim 4, wherein said crystallization is carried out in ethanol/water.

11. Process according to claim 5, wherein said metallic catalysts are selected from the group consisting of Pt, Pd and Ru.

12. Process according to claim 5, wherein said metallic catalysts are supported on a support chosen from the group consisting of carbon, silica gel, alumina and barium sulfate.

13. Process according to claim 5, wherein said metallic catalysts are in concentrations of 0.5 to 10% in moles with respect to the compound of formula (II).

14. Process according to claim 5, wherein said metallic catalysts are in concentrations of 0.5 to 10% in moles with respect to the compound of formula (III).

15. Process according to claim 6, wherein said dehydrogenation is performed at a temperature between 180° C. and 300° C.

16. Process according to claim 8, wherein said molar ratio is between 1:1 and 3:1.

17. Process according to claim 1, wherein said compound with formula (III) is dehydrogenated in a first reaction step in the absence of said easily reducible organic compound, and wherein said organic compound is added at the end of said first step in a molar ratio between 0.5:1 and 10:1, with respect to the compound wtih formula (III) that is initially present.

18. Process according to claim 17, wherein said molar ratio is between 1:1 and 3:1.

19. Process according to claim 1, wherein said dehydrogenation is achieved with a molar ratio between said compound with formula (II) and said easily reducible organic compound that is between 1:0.25 and 1:10.

20. Process according to claim 1, wherein said dehydrogenation is achieved with a molar ratio between said compound with formula (III) and said easily reducible organic compound that is between 1:0.25 and 1:10.

* * * * *